United States Patent [19]

Koziol et al.

[11] Patent Number: 4,666,446

[45] Date of Patent: May 19, 1987

[54] INTRAOCULAR LENS WITH CONVERGING AND DIVERGING OPTICAL PORTIONS

[76] Inventors: Jeffrey E. Koziol, 601 W. Central, Mount Prospect, Ill. 60056; Gholam A. Peyman, 535 N. Michigan Ave., Chicago, Ill. 60611

[21] Appl. No.: 860,291

[22] Filed: May 6, 1986

[51] Int. Cl.[4] .............................................. A61F 2/16
[52] U.S. Cl. ..................................................... 623/6
[58] Field of Search ........................................... 623/6

[56] References Cited

U.S. PATENT DOCUMENTS 4,074,368 2/1978 Levy et al. .............................. 623/6
4,581,031 4/1986 Koziol et al. .......................... 623/6

OTHER PUBLICATIONS

Ocular Surgery News, Jan. 15, 1986 edition, p. 14.
A New Approach to Macular Degeneration: A Low Vision System Utilizing an Iol of High Negative Power. (undated).
Donn, A. and Koester, an Ocular Telephoto System Designed to Improve Vision in Macular Disease, the CLAO Journal, vol. 12, No. 2, pp. 81-85, (April 1986).

Choyce, D. P., Intra-Ocular Lenses and Implants, London, 1964, pp. 156-161.

Primary Examiner—Richard J. Apley
Assistant Examiner—James Prizant
Attorney, Agent, or Firm—Roylance, Abrams, Berdo & Goodman

[57] ABSTRACT

An intraocular lens for patients having macular degeneration. The intraocular lens comprises a first portion including a diverging lens, and a second portion including a converging lens. The converging lens provides the patient with substantially the same vision he or she had prior to implantation of the intraocular lens, i.e., the decreased visual acuity normally associated with macular degeneration, while providing unmagnified and unrestricted peripheral vision. The diverging lens, when combined with converging lens means located outside the eye (e.g. a spectacle lens), provides a magnified retinal image of a given object with increased visual acuity but a restricted visual field. Thus, the intraocular lens of the invention provides the patient with the choice of unmagnified but peripherally unrestricted vision or magnified but peripherally restricted vision.

20 Claims, 15 Drawing Figures

INTRAOCULAR LENS WITH CONVERGING AND DIVERGING OPTICAL PORTIONS

FIELD OF THE INVENTION

This invention relates to intraocular lenses to be implanted in the eye upon removal of the natural lens for treatment of macular degeneration of the eye. The intraocular lens includes a converging lens that provides the patient with substantially the same vision he or she had prior to implantation of the intraocular lens, i.e., the decreased visual acuity normally associated with macular degeneration but with unmagnified vision and unrestricted field of vision. The intraocular lens also includes a diverging lens, which when combined with an external converging lens located outside and adjacent the eye, increases, i.e., magnifies, the retinal image size of a given object and improves visual acuity but provides a restricted field of vision. Thus, the invention provides the patient with the choice of unmagnified but peripherally unrestricted vision or magnified but peripherally restricted vision.

BACKGROUND OF THE INVENTION

A disease of the eye known as macular degeneration has become one of the leading causes of blindness in adults. This disease affects the central retinal area known as the macula which affords acute vision and receives light focused by the cornea and lens. This disease can lead to a gradual or sudden loss of vision to the level of 20/200 or less. Commonly, loss of vision only affects the central retinal area of about 0.25 to 4 square millimeters and does not usually progress beyond this area, thereby leaving 95–99% of the retina unaffected. Thus, reading and driving vision can be lost but peripheral vision remains intact.

Most cases of macular degeneration are untreatable, although laser photocoagulation has been some benefit in certain instances. Telescopic systems that attach to eye glasses also have been used for many years to improve vision in patients with macular degeneration. These systems, which work by increasing the retinal image size of a given object, however, have not been very successful because they restrict the visual field to about 11° so that normal activity is not possible. They are also large and bulky. Attempts have been made to increase the visual field by putting part of the telescope within the eye. A Galliean telescope is useful for this purpose and consists of a high converging objective lens and a high diverging ocular lens, which together produce a telescopic effect.

Recent publications by Charles Koester disclose that a high diverging lens can be implanted inside the eye and then high converging glasses are worn to provide a telescope having a significantly improved visual field of about 37°. A similar system was earlier described by Peter Choyce, who implanted a high diverging anterior chamber lens and used high converging spectacle glasses to create telescope in patients.

While the system described by both Koester and Choyce is an improvement over the prior spectacle-attached telescopes, it nevertheless has one inherent and severe drawback. The high minus intraocular lens implanted in the patient's eye is incapable of providing a focused retinal image by itself. It can only provide a focused retinal image when combined with an external converging spectacle lens, and then, the only image possible is a magnified image of reduced visual field.

The adjustment to such permanent magnification and reduced visual field is very difficult for patients since objects seem larger and thus appear closer and peripheral vision is severly restricted. Magnification may be fine for reading and other close work which use direct vision, but it is very burdensome for activities such as walking, shopping, etc., which can be comfortably carried out even with macular degeneration. Likewise, permanent reduction in peripheral vision restricts a person's activities.

Thus, there is a need for an ocular device which allows a patient to choose between magnified vision with decreased visual field, or the less acute vision normally associated with macular degeneration with unrestricted peripheral vision.

SUMMARY OF THE INVENTION

Accordingly, it is an object of this invention to provide an ocular device that will allow a patient to control his or her vision by choosing either magnified vision with decreased visual field or the vision normally associated with macular degeneration with unrestricted peripheral vision.

Another object of the invention is to provide an ocular device that allows a person with macular degeneration to switch from magnified more acute vision to unmagnified and unrestricted peripheral vision by merely removing spectacles.

The foregoing objects are basically accomplished by an intraocular lens adapted to be implanted in the eye, and used with an external converging spectacle lens to provide a magnified retinal image of a given object comprising an optical element having a first portion and a second portion, the first portion including a diverging lens, and the second portion including a converging lens; and means, coupled to the optical element, for supporting the optical element in the eye, wherein use of the intraocular lens in combination with the converging spectacle lens will provide a magnified retinal image of a given object while use of said intraocular lens without the converging spectacle lens will provide unmagnified and unrestricted peripheral vision.

Other objects, advantages and salient features of the present invention will become apparent from the following detailed description, which, taken in conjunction with the annexed drawings discloses a preferred embodiment of the invention.

BRIEF DESCRIPTION OF THE DRAWINGS

Referring now to the drawings which form a part of this original disclosure.

DETAILED DESCRIPTION OF THE INVENTION

Figure 1:
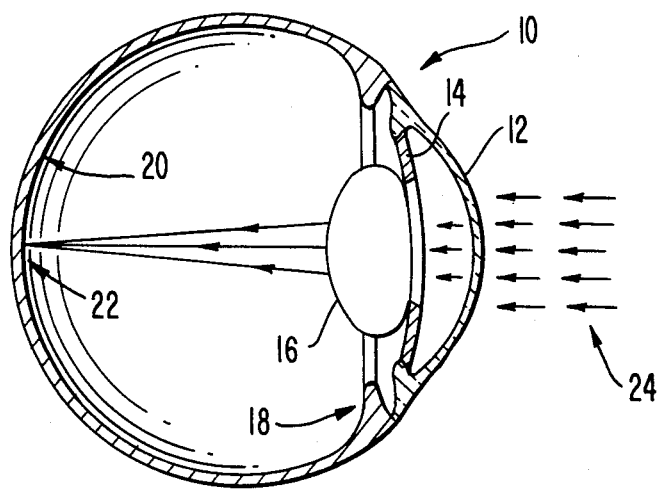
FIG. 1 is a side elevational view in longitudinal section of a schematic representation of a human eye including a natural lens.

As seen in FIG. 1, and eye 10 is shown including the cornea 12, iris 14, lens 16, the ciliary sulcus 18 adjacent the lens, the retina 20 and the macula 22.

As illustrated in FIG. 1, the macula 22 is located at the center of the retina 20 and is responsible for providing acute vision, such as that necessary for driving or reading. As seen in FIG. 1, light rays 24 are focused directly on the macula 22 by means of the cornea and the lines. The cornea has on the average 40 diopters of plus power and the lens has 20 diopters of plus power. This is equivalent to a very strong lens of 60 diopters. Thus, light rays 24 striking this system comprising the cornea and the lens substantially perpendicular to the eye are focused clearly on the macula 22 and provide acute vision, while light rays striking this system obliquely are unfocused and provide peripheral, less acute vision. However, when there is macular degeneration, visual acuity is decreased, thereby resulting in a blurred spot in the center of vision although less acute peripheral vision remains substantially the same.

Figure 2:
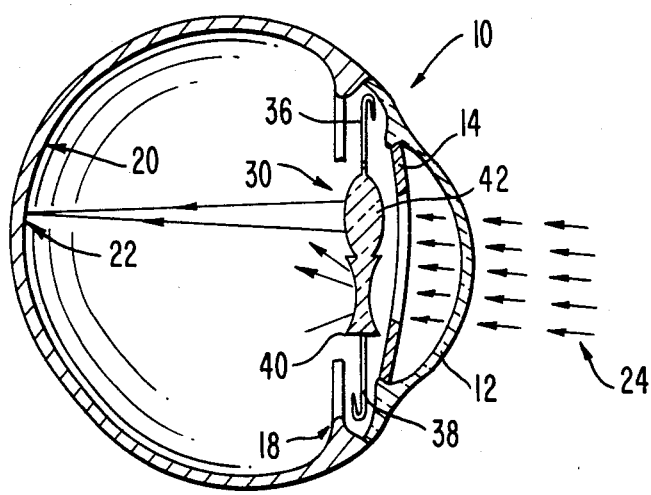
FIG. 2 is a side elevational view in longitudinal section similar to that shown in FIG. 1 except that the natural lens has been removed and an intraocular lens in accordance with the present invention has been implanted.
Figure 3:
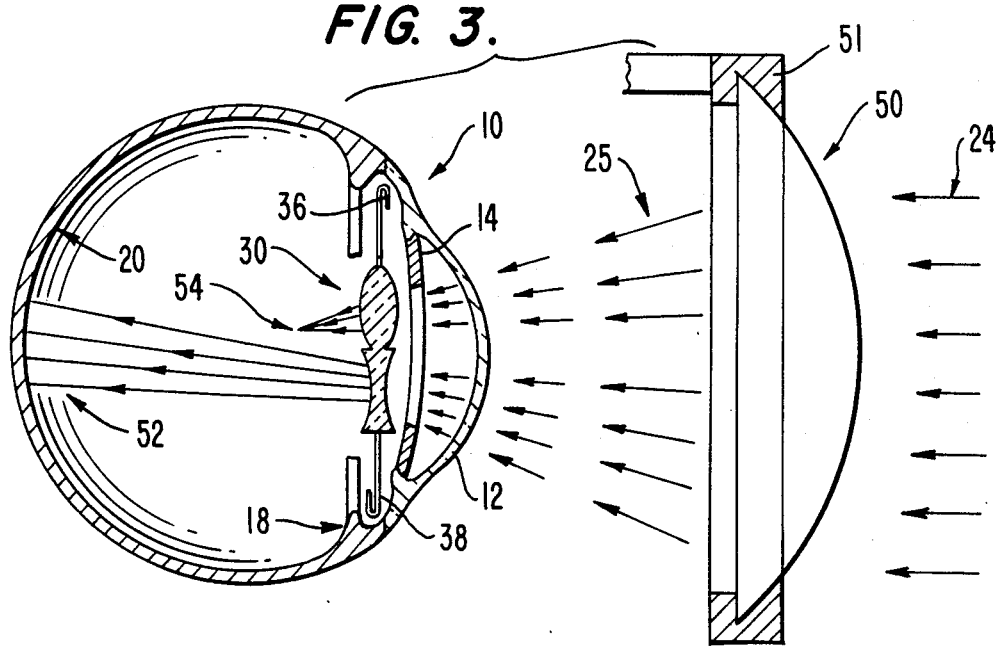
FIG. 3 is a side elevational view in longitudinal section similar to that shown in FIG. 2 except that converging lens means have been positioned outside the eye in accordance with the present invention.
Figure 4:
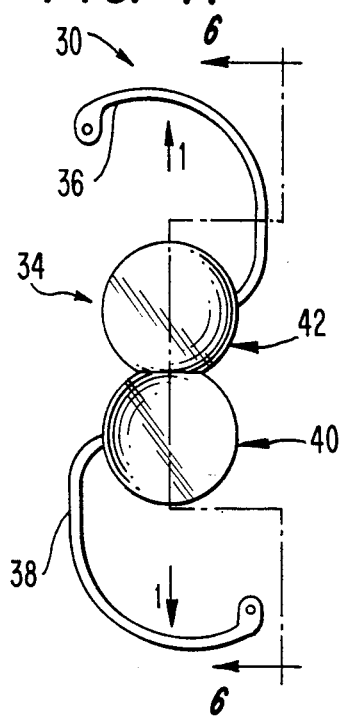
FIG. 4 is a front elevational view of the intraocular lens shown in FIGS. 2 and 3.
Figure 5:
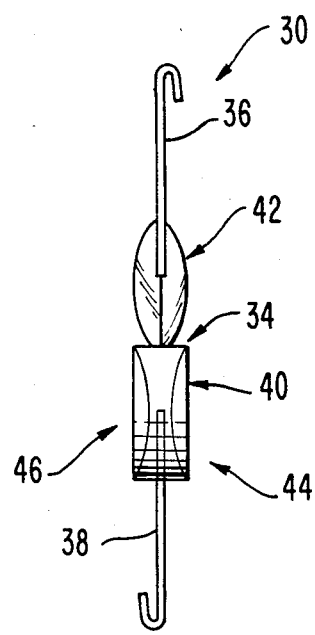
FIG. 5 is a right side elevational view in longitudinal section of the intraocular lens shown in FIGS. 2–4.
Figure 6:
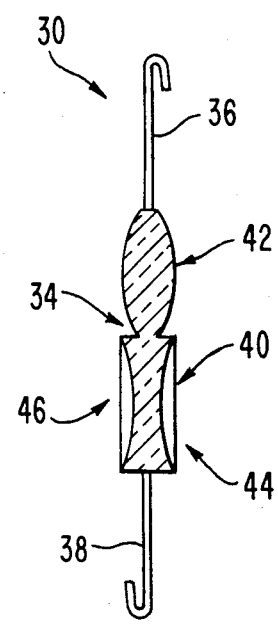
FIG. 6 is a right side elevational view of the intraocular lens of FIG. 4 taken along line 6—6 in FIG. 4.

Accordingly, the present invention as seen in FIGS. 2 and 3 comprises replacing the natural lens 16 with the intraocular lens 30 in accordance with the invention having both a diverging lens 40 and a converging lens 42. The converging lens 42 allows the patient to retain the same amount of peripheral vision but decreased visual acuity that he or she had prior to surgical implantation of the intraocular lens 30. The diverging lens, in combination with converging lens means located outside the eye (shown as spectacle lens 50 in FIG. 3), provides the patient with magnified and therefore more acute vision for activities such as reading, etc.

As seen in FIGS. 2-6, the intraocular lens 30 comprises an optical element 34 and a pair of haptic supports 36 and 38 integrally extending from the optical element. These supports do not have to be integrally formed with the optical element and can be coupled thereto in any suitable fashion, as long as they support the lens portion substantially centrally of the iris.

The optical element 34 can be ground or molded from suitable optical material such optical glass or polymeric material such as polymethylmethacrylate. This optical element comprises a first portion in the form of the diverging or negative lens 40 having a substantially concave outer surface on both the anterior and posterior sides 44 and 46, respectively, and a second portion in the form of the converging or positive lens 42 having a substantially convex outer surface on both the anterior and posterior sides 44 and 46. The lenses 40 and 42 are preferably integrally formed but they can be separately formed from the aforementioned materials and coupled in any suitable fashion.

The lenses 40 and 42 are shown positioned adjacent and substantially vertically aligned along center axis line 1—1. The outer peripheries of the lenses 40 and 42 are preferably circular, with the diverging lens 40 having a diameter of from 3 to about 4 mm and the converging lens 42 having a diameter of about 4 mm.

In use, the intraocular lens 30 is implanted in the eye 10 after the natural lens 16 is removed, with the supports 36 and 38 being located in the ciliary sulcus 18 to position the optical element 34 adjacent and behind the opening in the iris 14. Alternatively, the optical element 34 could be positioned in the anterior chamber of the eye, i.e., in front of the iris 14. As seen in FIG. 2, the light rays 24 pass through the cornea 12 and the iris 14 and strike the lenses 40 and 42 of the optical element 34. Light rays striking the diverging lens 40 will significantly diverge and thus will not present an image on the retinal surface. Light rays striking the converging lens 42, however, will be converged and will present a focused image on the retina.

It can be appreciated that the converging lens 42 functions substantially in the same manner as the surgically-removed natural lens 16, which is also a converging lens. Because of the similarity of the converging lens 42 and the natural lens 16, the patient will have substantially the same vision before and after implantation of the intraocular lens 30, characterized by decreased visual acuity and a center of vision that is blurred. However, vision is unmagnified and peripheral vision is unrestricted to enable many normal activities such as walking, shopping, etc.

When the patient desires to perform activities such as reading and spotting objects in the distance, magnification is needed to increase acuity, although it also restricts the visual field. The patient can obtain magnified vision by simply positioning a converging lens means outside the eye as shown in FIG. 3. As shown in FIG. 3, the converging lens means is preferably a spectacle lens 50 housed in spectacle frame 51. The converging spectacle lens 50 causes the light rays 24 to converge and enter the eye 10 through cornea 12 and iris 14. The converging light rays 25 then strike the lenses 40 and 42 of the intraocular lens 30. Light rays striking the diverging lens 40 will be diverged to produce a magnified retinal image 52 on the retina 20. This combination of a converging lens and diverging lens is known as a Galilean telescope. The converging light rays striking the converging lens 42 will be further converged to a focal point 54 immediately behind the lens 42, and will thus be obscured. By this method, the patient can remove and replace the converging spectacle lens to switch from a normal to a telescopic system and thus have control over his or her magnification and visual field.

The diverging lens 40 of the optical element 34 will normally have a power of from about minus 40 to about minus 70, and the converging lens 42 will normally have a power of from about plus 10 to about plus 22. The converging lens means (e.g., spectacle lens) will normally have a power of from about plus 25 to about plus 35. The mgnification provided by the above-described lenses can range from about 2X to about 4X, depending on the power and vertex distance of the spectacle lens. The field of vision will also range from about 35° to about 45°, depending upon the magnification selected.

EMBODIMENT OF FIGS. 7–9

Figure 7:
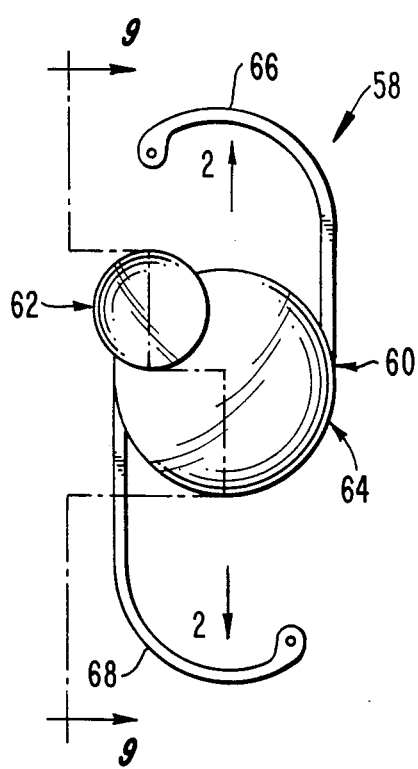
FIG. 7 is a front elevational view of a second embodiment of an intraocular lens in accordance with the invention.
Figure 8:
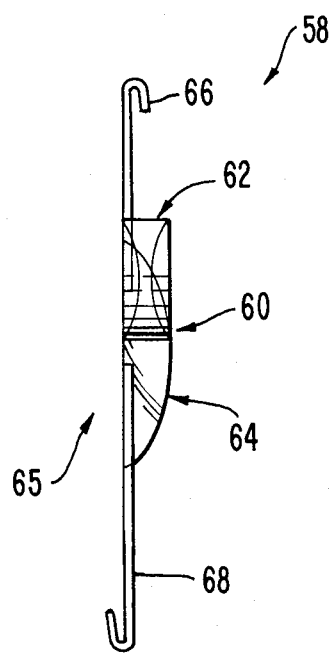
FIG. 8 is a left side elevational view of the intraocular lens shown in FIG. 7.
Figure 9:
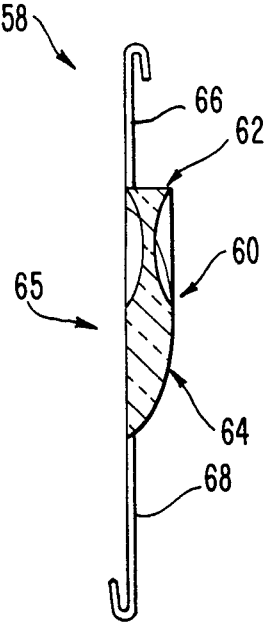
FIG. 9 is a left side elevational view in longitudinal section of the intraocular lens of FIG. 7 taken along line 9—9 in FIG. 7.

A second embodiment of an intraocular lens in accordance with this invention is shown in FIGS. 7–9. The intraocular lens 58 is similar to intraocular lens 30 shown in FIGS. 2–6, in that the optical element 60 comprises first and second portions 62 and 64 that are in the form of a diverging lens and a converging lens and that are positioned adjacent one another, but the first portion 62 is smaller in diameter, partially received in the second portion, and laterally offset from vertical center axis line 2—2. The first portion will normally range in the size from about 3 to about 4 mm, while the second portion will range in size from about 4 to about 6 mm. In this embodiment, the posterior surface 65 of the second portion 64 is substantially flat, and the haptic supports 66 and 68 are both coupled to the second portion 64 so as to be substantially coplanar with its posterior surface 65. Alternatively, it is contemplated that the second portion could be smaller in diameter than the first portion and laterally offset from a vertical center axis line running through the first portion. Other variations of optical elements having adjacent first and second portions are also contemplated by this invention, including for example, substantially equally sized first and second portions that are positioned substantially laterally adjacent along a horizontal center axis line.

EMBODIMENTS OF FIGS. 10–15

Figure 10:
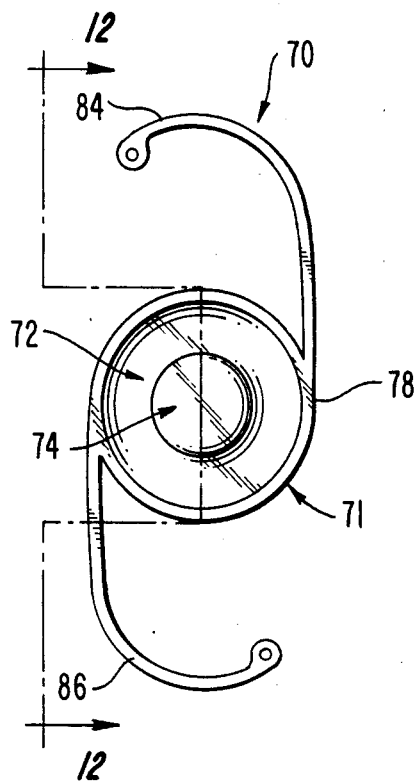
FIG. 10 is a front elevational view of a third embodiment of an intraocular lens in accordance with the invention.
Figure 11:
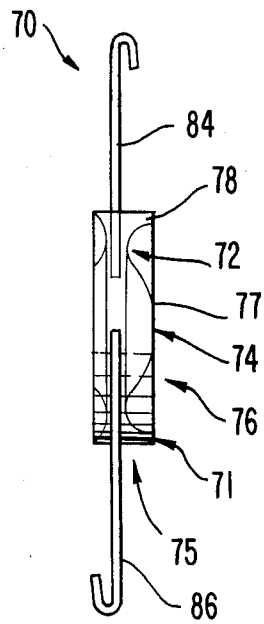
FIG. 11 is a left side elevational view of the intraocular lens shown in FIG. 10.
Figure 12:
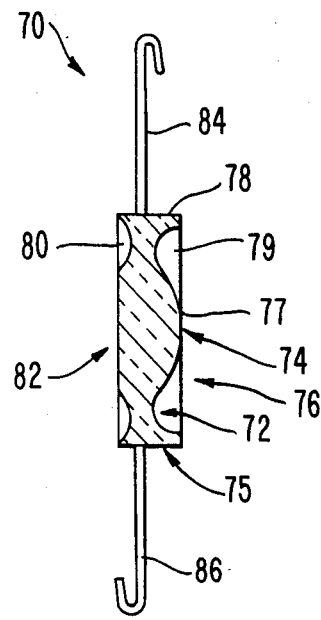
FIG. 12 is a left side elevational view in longitudinal section of the intraocular lens of FIG. 10 taken along line 12—12 in FIG. 10.
Figure 13:
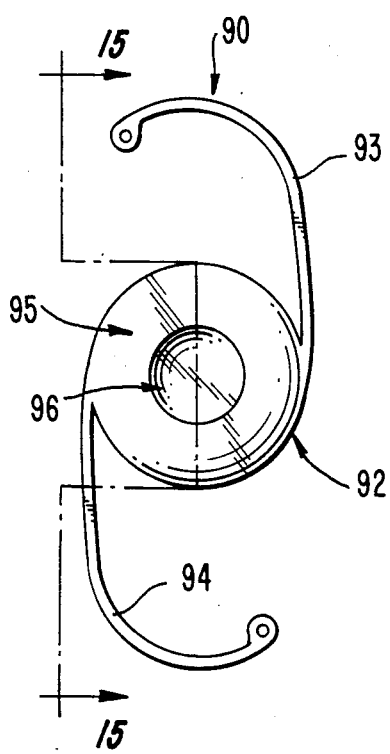
FIG. 13 is a front elevational view of a fourth embodiment of an intraocular lens in accordance with the invention.
Figure 14:
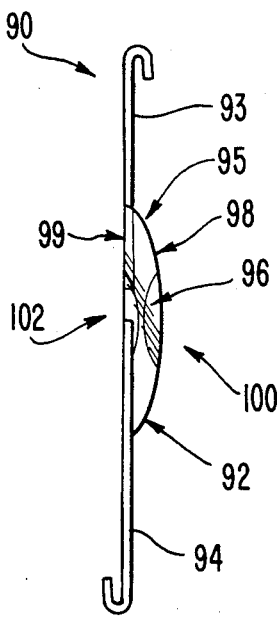
FIG. 14 is a left side elevational view of the intraocular lens shown in FIG. 13.
Figure 15:
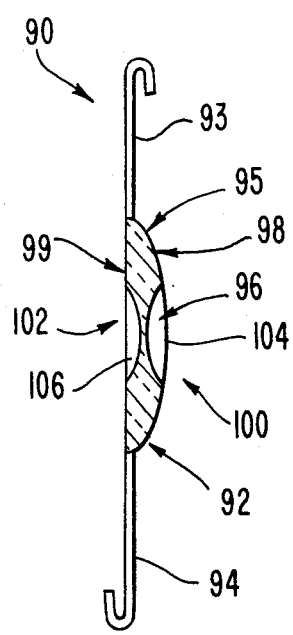
FIG. 15 is a left side elevational view in longitudinal section of the intraocular lens of FIG. 13 taken along line 15—15 in FIG. 13.

FIGS. 10–15 illustrate two additional embodiments of intraocular lenses that can be used in accordance with this invention. These intraocular lenses are similar to that shown in FIG. 1, but instead of adjacent and aligned first and second portions, the second portion is substantially centrally located within the first portion, as shown in FIGS. 10–12, or the first portion is substantially centrally located within the second portion, as shown in FIGS. 13–15.

In FIGS. 10–12, intraocular lens 70 comprises an optical element 71 and a pair of haptic supports 84 and 86 attached thereto. The optical element 71 has a substantially cylindrical peripheral surface 75 and comprises a second portion 74 substantially centrally located within first portion 72. Around the periphery of the anterior side 76 is an annular lip 78. Radially inward from lip 78 and on the anterior side is an annular concave surface 79 of first portion 72. The first portion 72 also includes a second annular concave surface 80 on the posterior side 82. Annular surfaces 79 and 80 form a diverging lens and have substantially semieliptical cross sections, with annular surface 80 being slightly smaller than annular surface 79. The inner side of annular surface 79 defines an outwardly facing convex surface 77 that is part of the converging lens included in second portion 74. The posterior side of the second portion 74 is substantially flat.

FIGS. 13–15 illustrate another embodiment of an intraocular lens 90 in accordance with this invention. In this embodiment, intraocular lens 90 is comprised of optical element 92 and a pair of haptic supports 93 and 94. The optical element 92 comprises first portion 96 substantially centrally located within the second portion 95. The outer surface of second portion 95 is defined by a substantially outwardly facing convex surface 98 on the periphery of the anterior side 100 and a substantially flat surface 99 on the periphery of the posterior side 102, thereby forming a converging lens. The first portion 96 is substantially centrally located within the second portion 95 and has substantially outwardly facing concave surfaces on both the anterior and posterior sides 100 and 102, defining substantialy equally sized recesses 104 and 106 having substantially semieliptical cross sections, thereby forming a diverging lens.

The diverging and converging lenses included in the intraocular lenses shown in FIGS. 7–15 focus light rays in substantially the same manner as diverging and converging lenses included in intraocular lens 30 shown in FIGS. 2–6.

While four advantageous embodiments have been chosen to illustrate the invention, it will be understood by those skilled in the art that various changes and modifications can be made therein without departing from the scope of the invention as defined in the appended claims. For example, rather than forming the first and second portions integrally as one piece, they could be formed separately and then rigidly coupled together.

What is claimed is:

1. An intraocular lens adapted to be implanted in the eye, and used with an external converging spectacle lens to provide a magnified retinal image of a given object, comprising:
    an optical element having a first portion and a second portion,
        said first portion including a diverging lens, and
        said second portion including a converging lens,
            said converging and diverging lenses being offset from each other in a direction perpendicular to the optical axis of the eye; and
    means, coupled to said optical element, for supporting said optical element in the eye,
    wherein use of said intraocular lens in combination with the converging spectacle lens will provide a magnified retinal image of a given object, while use of said intraocular lens without the converging spectacle lens will provide unmagnified and unrestricted peripheral vision.

2. An intraocular lens according to claim 1, wherein said diverging lens has a power of from about minus 40 to about minus 70.

3. An intraocular lens according to claim 1, wherein said converging lens has a power of from about plus 10 to about plus 22.

4. An intraocular lens according to claim 2, wherein said converging lens has a power of from about plus 10 to about plus 22.

5. An intraocular lens according to claim 1, wherein said first portion and said second portion are integrally formed.

6. An intraocular lens according to claim 1, wherein said first portion is positioned substantially adjacent to said second portion.

7. An intraocular lens according to claim 1, wherein said first portion is located substantially within said second portion.

8. An intraocular lens according to claim 1, wherein said second portion is located substantially within said first portion.

9. An optical system capable of providing a patient having macular degeneration with the reversible choice of having the decreased visual acuity characteristic of the patient's macular degeneration but unmagnified and unrestricted peripheral vision, or having more acute but magnified vision, comprising:
an optical element having a first portion and a second portion,
said first portion including a diverging lens, and
said second portion including a converging lens,
said converging and diverging lenses being offset from each other in a direction perpendicular to the optical axis of the eye;
means, coupled to said optical element, for supporting said optical element in the eye; and
converging lens means capable of being located outside and adjacent the eye for focusing light into the eye, in combination with said diverging lens in said optical element, to provide the patient with a magnified retinal image of a given object,
wherein when said converging lens means is located outside and adjacent the eye, the patient will have more acute but magnified vision, and when said converging lens means is not located adjacent the eye, the patient will have the decreased visual acuity characteristic of the patient's macular degeneration but unmagnified and unrestricted peripheral vision.

10. An optical system according to claim 9, wherein said converging lens means is a spectacle lens.

11. An optical system according to claim 10, wherein said spectacle lens has a power of from about plus 25 to about plus 35.

12. An optical system according to claim 9, wherein said diverging lens has a power of from about minus 40 to about minus 70.

13. An optical system according to claim 9, wherein said converging lens has a power of from about plus 10 to about plus 22.

14. An optical system according to claim 11, wherein
said diverging lens has a power of from about minus 40 to about minus 70, and
said converging lens has a power of from about plus 10 to about plus 22.

15. An optical system according to claim 9, wherein said first portion and said second portion are integrally formed.

16. An optical system according to claim 9, wherein said first portion is positioned substantially adjacent to said second portion.

17. A optical system according to claim 9, wherein said first portion is located substantially within said second portion 18. An optical system according to claim 9, wherein said second portion is located substantially within said first portion.

19. An optical system according to claim 9, wherein said optical element is formed of glass.

20. An optical system according to claim 9, wherein said optical element is formed of a polymeric material.

* * * * *